US011666313B1

(12) United States Patent
Minkoff (10) Patent No.: US 11,666,313 B1
(45) Date of Patent: Jun. 6, 2023

(54) CALIBRATION TECHNIQUE, APPARATUS AND SYSTEM FOR PULSED PHASE-LOCK LOOP ULTRASOUND INTRACRANIAL PRESSURE MEASUREMENT SYSTEMS

(71) Applicant: Fonar Corporation, Melville, NY (US)

(72) Inventor: Lawrence A. Minkoff, Westfield, NJ (US)

(73) Assignee: Fonar Corporation, Melville, NY (US)

( * ) Notice: Subject to any disclaimer, the term of this patent is extended or adjusted under 35 U.S.C. 154(b) by 161 days.

(21) Appl. No.: 17/111,599

(22) Filed: Dec. 4, 2020

(51) Int. Cl.
| | |
|---|---|
| G01L 11/06 | (2006.01) |
| G01L 27/00 | (2006.01) |
| G01N 29/00 | (2006.01) |
| A61B 5/03 | (2006.01) |
| A61B 8/00 | (2006.01) |
| A61B 8/08 | (2006.01) |

(52) U.S. Cl.
CPC .............. *A61B 8/587* (2013.01); *A61B 5/031* (2013.01); *A61B 8/0808* (2013.01); *G01L 11/06* (2013.01); *G01L 27/005* (2013.01); *G01N 2291/02872* (2013.01)

(58) Field of Classification Search
CPC .......... G01L 11/04; G01L 11/06; G01L 27/00; G01L 27/002; G01L 27/005; G01N 2291/02872; G01B 21/042; A61B 8/58; A61B 8/582; A61B 8/585; A61B 8/587; A61B 5/031
See application file for complete search history.

(56) References Cited

U.S. PATENT DOCUMENTS

| | | | | | |
|---|---|---|---|---|---|
| 3,927,369 | A | * | 12/1975 | Billeter | .................... G01K 5/52 |
| | | | | | 324/636 |
| 4,003,141 | A | * | 1/1977 | Le Roy | ................... A61B 5/031 |
| | | | | | 434/270 |
| 4,945,768 | A | * | 8/1990 | Sorrells | .................... G01L 11/04 |
| | | | | | 73/717 |

(Continued)

FOREIGN PATENT DOCUMENTS

| | | | | |
|---|---|---|---|---|
| EP | 3278735 A1 | * | 2/2018 | ......... A61B 5/02156 |
| JP | H062701 A | * | 1/1994 | |
| KR | 100969503 B1 | * | 7/2010 | |

OTHER PUBLICATIONS

Kuchiwaki et al., Human Dural Thickness Measured by Ultrasonographic Method: Reflection of Intracranial Pressure, J Ultrasound Med, 1997, 725-730, 16, American Institute of Ultrasound in Medicine, USA.

(Continued)

*Primary Examiner* — Herbert K Roberts
(74) *Attorney, Agent, or Firm* — Lerner David LLP (57) ABSTRACT

A calibration system for a pulsed phase-lock loop ultrasound measurement system comprising an apparatus having a compartment for holding a pressure sensitive liquid. The compartment has an opening by which a flow of the pressure sensitive liquid may be controlled. A sensor arranged relative to the compartment to receive ultrasonic signals that reflect off one or more inner surfaces of the compartment. The system includes a processing device for receiving an integrated error signal output by the sensor based on pressure changes of the pressure sensitive liquid responsive to a change in flow of pressure sensitive liquid between the source and the compartment.

20 Claims, 12 Drawing Sheets

(56) References Cited

U.S. PATENT DOCUMENTS

| | | | | |
|---|---|---|---|---|
| 5,214,955 | A * | 6/1993 | Yost | G01N 29/075 |
| | | | | 73/61.79 |
| 5,325,339 | A * | 6/1994 | Yost | G01N 29/30 |
| | | | | 367/13 |
| 5,387,194 | A * | 2/1995 | Williams | A61B 1/00048 |
| | | | | 604/920 |
| 5,617,873 | A * | 4/1997 | Yost | A61B 8/0808 |
| | | | | 33/511 |
| 6,413,227 | B1 * | 7/2002 | Yost | A61B 5/031 |
| | | | | 600/561 |
| 6,475,147 | B1 * | 11/2002 | Yost | A61B 8/0808 |
| | | | | 600/438 |
| 6,761,695 | B2 * | 7/2004 | Yost | A61B 5/031 |
| | | | | 600/561 |
| 6,773,407 | B2 * | 8/2004 | Yost | A61B 8/0808 |
| | | | | 600/300 |
| 10,390,704 | B2 * | 8/2019 | Yost | A61B 5/7246 |
| 2003/0060711 | A1 * | 3/2003 | Michaeli | A61B 8/0808 |
| | | | | 600/451 |
| 2003/0191410 | A1 * | 10/2003 | Yost | A61B 8/0808 |
| | | | | 600/561 |
| 2006/0025686 | A1 * | 2/2006 | Ueno | A61B 8/08 |
| | | | | 600/443 |
| 2006/0079773 | A1 * | 4/2006 | Mourad | A61B 5/031 |
| | | | | 600/438 |
| 2010/0071473 | A1 * | 3/2010 | Dowalo | G01M 3/3272 |
| | | | | 73/744 |
| 2015/0168243 | A1 * | 6/2015 | Smith | G01L 11/06 |
| | | | | 73/703 |
| 2016/0331949 | A1 * | 11/2016 | Lutz | A61M 27/006 |
| 2017/0160175 | A1 * | 6/2017 | Al-Mayah | A61B 5/6853 |
| 2017/0238827 | A1 * | 8/2017 | Seba | A61B 5/0002 |
| 2018/0242945 | A1 * | 8/2018 | Tomoeda | A61B 5/02208 |
| 2018/0321103 | A1 * | 11/2018 | Johansen | G01L 9/0076 |
| 2020/0315583 | A1 * | 10/2020 | Baumann | A61B 8/4272 |

OTHER PUBLICATIONS

Ueno et al., Cranial Diameter Pulsations Measured by Non-Invasive Ultrasound Decrease with Tilt, Aviation, Space, and Environmental Medicine, Aug. 2003, 882-885, 74:8.

Ueno et al., Noninvasive assessment of intracranial pressure waveforms by using pulsed phase lock loop technology, Journal of Neurosurgery, Aug. 2005, 361-367, 103.

Ueno et al., Noninvasive Measurement of Pulsatile Intracranial Pressure Using Ultrasound, Acta Neurochir, 1998, 66-69, 71(Suppl).

Webster, A Pulsed Ultrasonic Distance Measurement System based upon Phase Digitizing, IEEE Transactions on Instrumentation and Measurement, Aug. 1994, 578-582, 43:4.

Yost et al., Fundamental aspects of pulse phase-locked loop technology-based methods for measurement of ultrasonic velocity, The Journal of the Acoustical Society of America, Mar. 1992, 1456-1468, 91:3, USA.

* cited by examiner

CALIBRATION TECHNIQUE, APPARATUS AND SYSTEM FOR PULSED PHASE-LOCK LOOP ULTRASOUND INTRACRANIAL PRESSURE MEASUREMENT SYSTEMS

BACKGROUND

Elevated intracranial pressure (ICP) is regarded as a sign of neurological deterioration in patients with head trauma, cerebrovascular, and neurodegenerative diseases. ICP is also considered important in long term space flight as many astronauts suffer from vision degeneration when exposed to micro-gravity over long durations. Such vision issues may be related to changes in fluid balance with increased ICP.

A technique for non-invasive measurement of ICP uses ultrasonic signals to measure ICP waveforms. The technique is often referred to as pulsed phase-lock loop ("PPLL") ultrasound. The technique relies upon detection of skull movements that are known to take place in relation to fluctuations or changes in ICP. It has been demonstrated that the skull moves on the order of a few microns in association with changes of ICP. The development of PPLL makes it possible to measure small variations in distance including down to the micron range. This makes it possible to measure changes in the size of the skull during a single cardiac cycle and calculation of a subject's ICP. Typically, the PPLL technique or instrument transmits an ultrasonic tone burst through the cranium using a transducer, e.g., an ultrasound sensor, placed on the head. The ultrasonic wave passes through the cranial cavity, reflects off the inner surface of the other side of the skull, and is detected and received by the transducer. The PPLL equipment compares the phase of emitted and received waves and alters the transmitted frequency of subsequent signal transmissions to maintain a constant phase difference, e.g., 90°, between the transmitted and received signals. Calibration of the PPLL is accomplished by the very nature of the ultrasound tone. A change in distance can be calculated by a change in phase that is received. Further, this can be checked by using an ultrasound target that can be moved a precise, small distance.

SUMMARY

Given the micron scale involved in ICP measurements, calibration of PPLL equipment, e.g., testing and adjustment of such equipment against a known standard, is important. An aspect of the disclosed technology of this is application is provision of method, apparatus and system that can be used to calibrate PPLL equipment. The apparatus emulates skull movement and allows PPLL operators to check their PPLL equipment against a known, controllable standard.

An aspect of the disclosed technology comprises a calibration system for a pulsed phase-lock loop ultrasound measurement system. The system may comprise an apparatus having a compartment for holding a liquid, the compartment having an opening by which a flow of the liquid may be controlled; a sensor arranged relative to the compartment to receive ultrasonic signals that reflect off one or more inner surfaces of the compartment; and a pressure gauge for measuring pressure of the liquid responsive to a change in flow of liquid between the source and the compartment. The system may also comprise a processing device for receiving an integrated error signal output by the sensor based on pressure changes of the liquid responsive to a change in flow of liquid between the source and the compartment.

The system may also comprise a pump coupled to a source of liquid. The pump may comprise a syringe. Further, the pump and pressure gauge may be coupled to a controller, the controller controlling the timing of the pump to increase or decrease the pressure of the liquid in accordance with a cardiac cycle of a subject. The controller may comprise the processing device. The controller may also comprise a second processing device distinct from the processing device.

In addition, the compartment of the apparatus is fitted with a balloon that holds the liquid. The compartment may be contoured to restrict movement of the balloon that holds the liquid in one direction relative to a side of the apparatus. In this regard, movement of the balloon may be restricted in a direction orthogonal to a base of the apparatus. The compartment of the apparatus may comprise a pair of side walls, a top and a bottom, the bottom including an area having a thin flexible membrane seal. The sensor may be arranged proximate the thin flexible membrane seal. The top may comprise a rigid seal around the periphery of the apparatus, the rigid seal supporting a flexible expandable material. In addition, the flexible expandable material may comprise a material having elasticity that is equivalent to that of a human skull. The flexible expandable material moving in response to pressure changes in the pressure sensitive liquid.

The pressure gauge may comprise a pressure sensor having a voltage output signal, and the processing device correlates pressure changes indicated by the voltage output signal to a change in distance caused by movement of the liquid. The processing device correlating the change in distance to the integrated error output signal to calibrate the sensor.

In another aspect, the disclosed technology may comprise a process or a method for calibrating a pulsed phase-lock loop ultrasound measurement system comprising causing pressure changes to a liquid housed in a compartment; detecting, by a sensor, ultrasonic signals that reflect off one or more inner surfaces of the compartment, the ultrasonic signals having information responsive to the pressure; measuring pressure of the liquid responsive to the pressure changes; measuring one or more changes in distance associated with the liquid caused by the pressure changes; and processing, based on pressure changes of the liquid and the measured one or more changes in distance, an integrated error signal output by the sensor to calibrate the sensor.

Causing pressure changes may comprise increasing or decreasing the pressure of the liquid by increasing or decreasing the flow of liquid into or out of the compartment. Further, causing pressure changes comprises increasing or decreasing the pressure of the liquid in accordance with a cardiac cycle of a subject. Further still, processing may comprise calculating one or more distance values based on the integrated error signal and comparing the measured one or more changes in distance to at least one calculated distance value of the one or more calculated distance values.

DESCRIPTION

Figure 1:
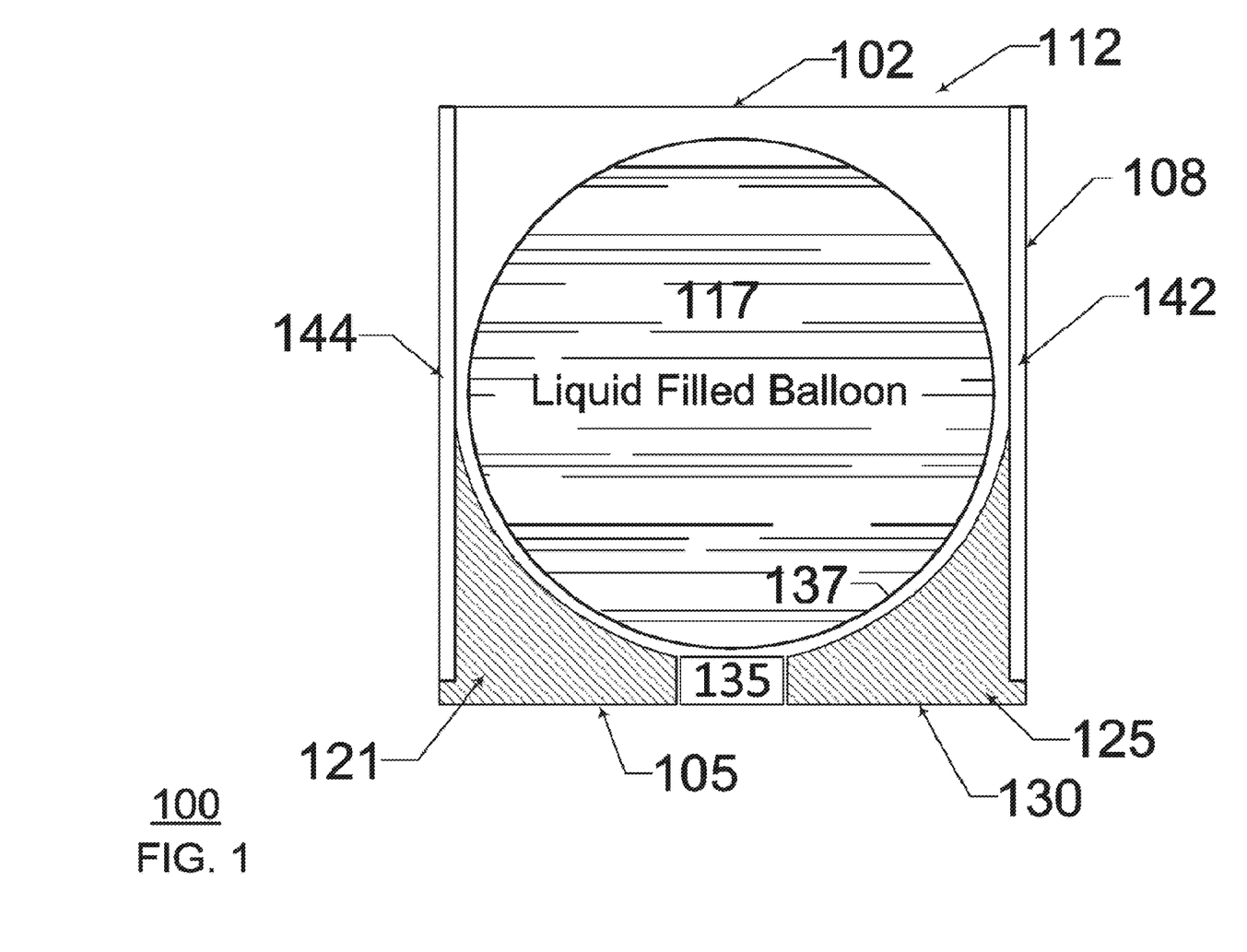
FIG. 1 is an example apparatus or system in accordance with one or more aspects of the disclosed technology.

FIG. 1 shows an example system 100 in accordance with one or more aspects of the present technology. The system includes a generally rectangular apparatus 108 having a tubular opening 112. The apparatus 108 is shown in side view along a plane extending from a top surface or end 102 of the apparatus towards a base, bottom, or lower end 105. The apparatus 108 typically forms a closed compartment. A liquid filled balloon 117 is located within the opening 112. The liquid within balloon 117 may comprise water or other liquid of a known viscosity, including for example, alcohol, mineral oil, motor oil, etc. The apparatus includes a plurality of support structures 121, 125 positioned beneath balloon 117. Support structures 121, 125 may form a base, bottom or lower end 105 of apparatus 108. Support structures are arranged to provide an opening for an ultrasound sensor 135 placed beneath balloon 117. Support structures 121, 125 also serve as a rigid support for a surface 137 of balloon 117 oriented toward base 130 of apparatus 108. Apparatus 108 also includes side surfaces 140, 144 that define tubular opening 112 and the generally rectangular shape of apparatus 108. In operation, sensor 135 measures the distance from the bottom to the top of balloon 117.

Figure 2:
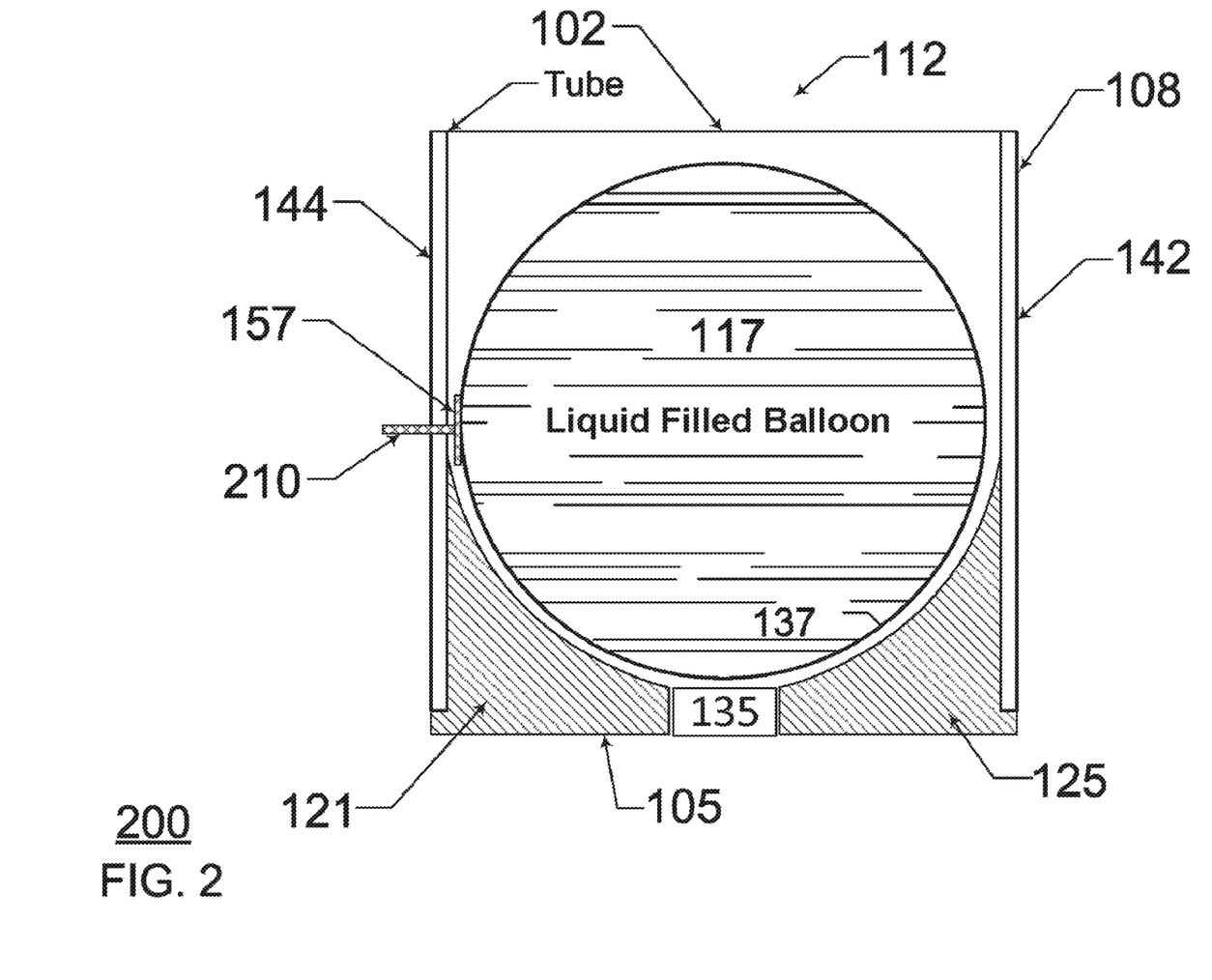
FIG. 2 is an example apparatus or system in accordance with one or more aspects of the disclosed technology.
Figure 3:
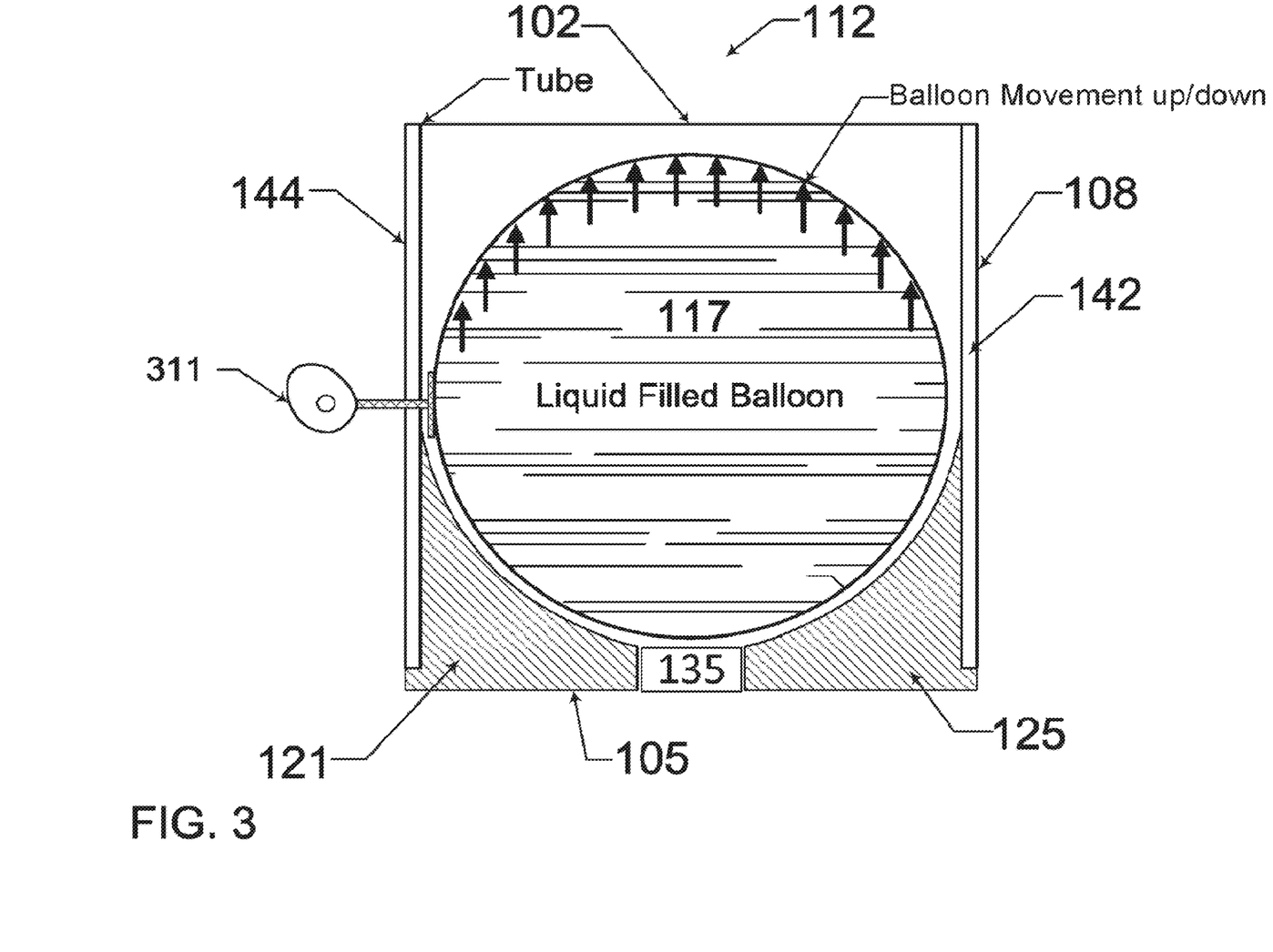
FIG. 3 is an example apparatus or system in accordance with one or more aspects of the disclosed technology.

FIG. 2 shows an example system 200 in accordance with one or more aspects of the present technology. Components or structures of system 200 with like reference numerals as those labelled in FIG. 1 comprise the same component or structures to those described in relation to FIG. 1 and having the same reference numeral. And their description is not repeated in relation FIG. 2 unless necessary. FIG. 2 includes a piston 210 arranged to push against a side surface 157 of balloon 117. As a force F is applied to piston 210 towards balloon 117, the shape of the balloon is decreased laterally forcing the balloon to increase vertically, increasing the distance from the bottom to the top of balloon 117 as shown in FIG. 3. The direction of expansion of balloon 117 is controlled by placement of support structures 121, 125 at the base 105 to prevent downward movement of the balloon 117. As balloon 117 when filled with a liquid forms a spherical outer surface, support structures 121, 125 form a basin like structure at the base of apparatus 108.

Movement of piston 210 may be controlled by a camshaft 311 on a variable speed electric motor. Adjusting the size of the cam 311 may be used to control an amount of piston movement, which in turn would increase or decrease the length of balloon 117, e.g., the distance between the top of the balloon and the bottom of the balloon at the base. This change in distance may be correlated to a change in pressure within balloon 117.

Figure 4:
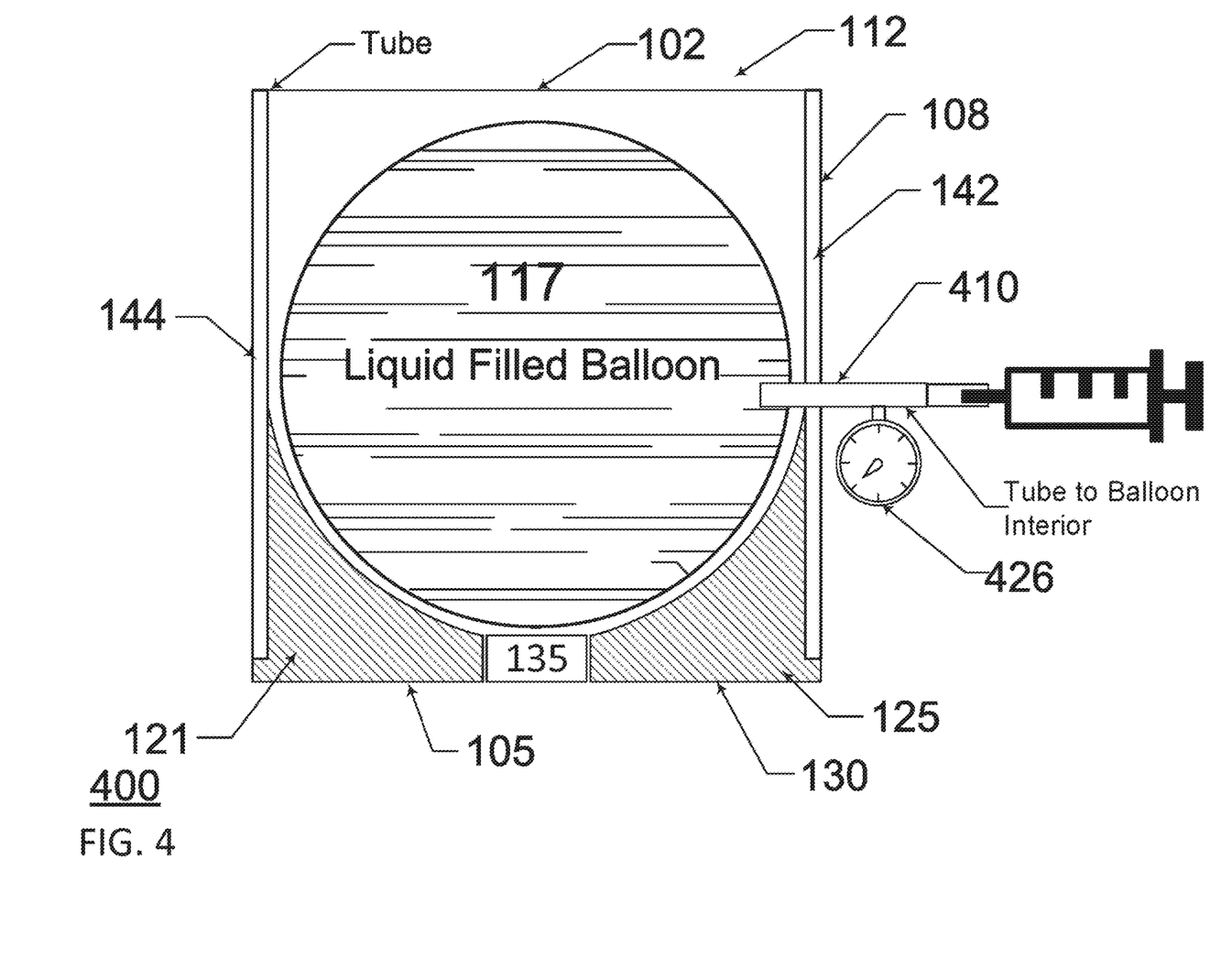
FIG. 4 is an example apparatus or system in accordance with one or more aspects of the disclosed technology.

FIG. 4 shows an example of an alternative system 400 in accordance with additional aspects of the disclosed technology. In system 400, a tube 410 is inserted through a sidewall 142 (any sidewall would suffice) of apparatus 108. The tube 410 is filled with the liquid that also fills balloon 117. The tube 410 is coupled to a syringe pump 418 and a pressure gauge 426. Pump 418 can be used to increase the volume of liquid to cause the distance between the top of the balloon and the bottom of the balloon at the base to change. Pressure gauge 426 may then be used to measure the change in pressure within the balloon and that may be correlated to the change in distance of upward movement of the balloon as measured by the sensor 135. These measurements can be used to calculate the elastance of the balloon material. For example, if pressure gauge 426 comprises a pressure sensor with a voltage output, that voltage output may then be used to compare pressure changes with the upward movement of the balloon and the output of the ultrasound sensor 135. The comparison may then serve as a calibration measure for the sensor 135 such that when measuring ICP, pressure changes can be more accurately correlated to changes in skull size.

Figure 5:
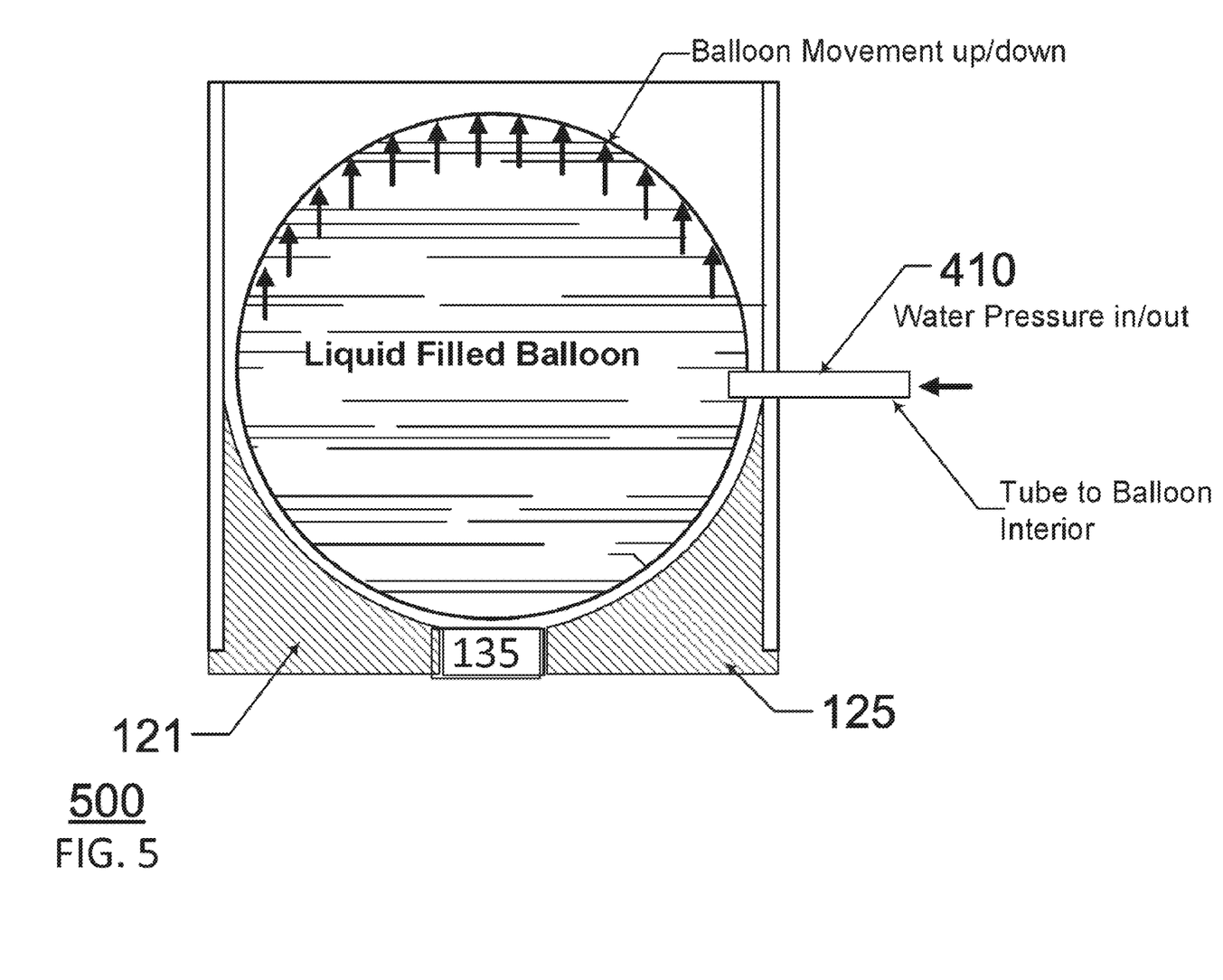
FIG. 5 is an example apparatus or system in accordance with one or more aspects of the disclosed technology.

FIG. 5 depicts the movement of balloon 117 in the system of FIG. 4 as the volume of liquid or water within balloon 117 is changed using syringe 418. As shown in FIG. 5, the expansion of the balloon is restricted to upward movement due to restrictions at the side and bottom of balloon 117. The flow of liquid into and out of balloon 117 may be computer controlled by coupling the syringe, or alternatively a pump, to a processing device that times the settings for increasing and decreasing the pressure so that they mimic one or more cardiac cycles associated with a subject whose ICP would be measured using sensor 135.

Figure 6:
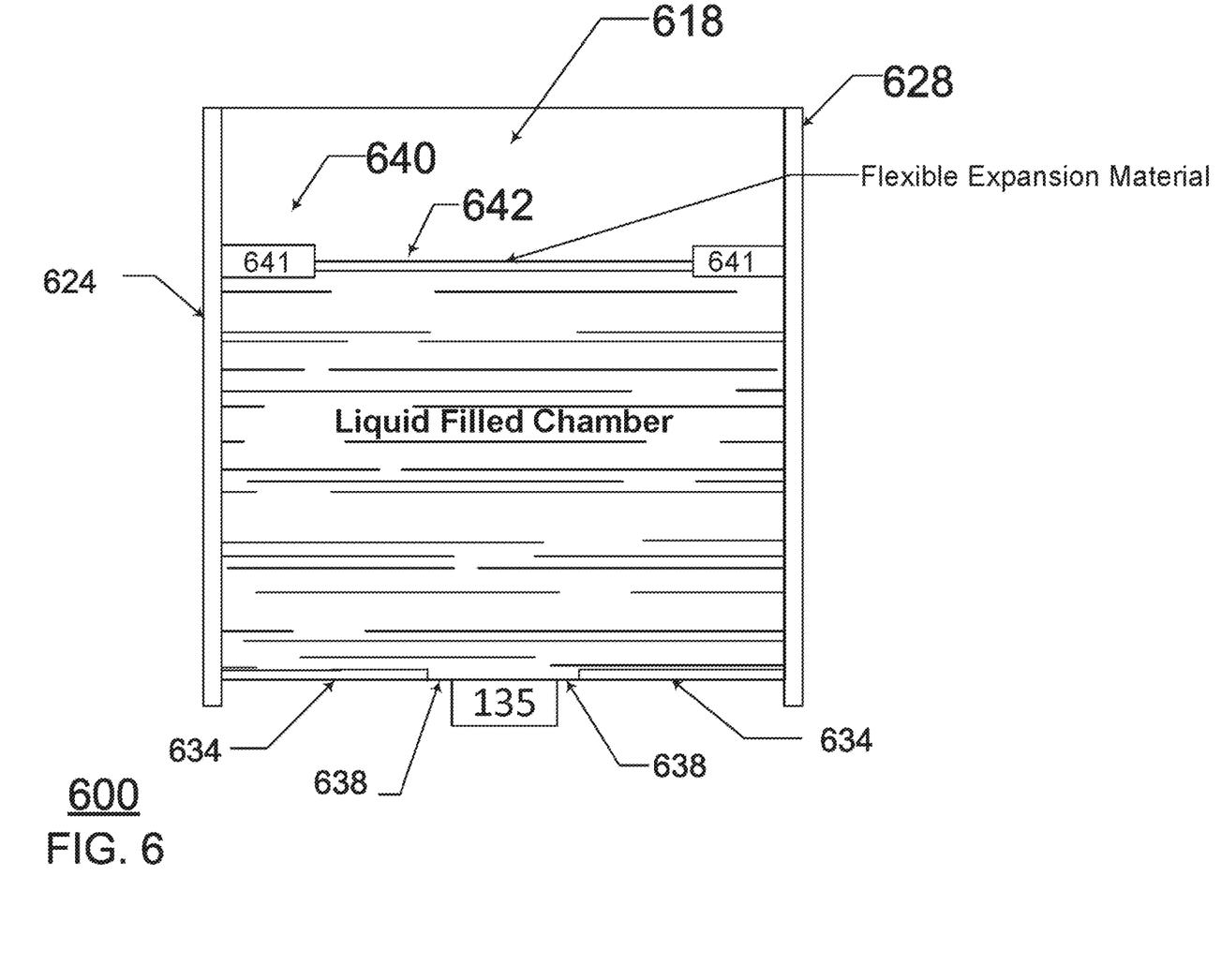
FIG. 6 is an example apparatus or system in accordance with one or more aspects of the disclosed technology.

FIG. 6 shows a system 600 in accordance with one or more aspects of the disclosed technology. FIG. 6 includes apparatus 610, which includes chamber 618, formed by side walls 624, 628, bottom or base 634, and top 640. Bottom 634 is rigid except for window 638, which comprises a thin flexible membrane seal. Sensor 135 is arranged proximate window 638 so to cover the sensor 635 relative to the interior or chamber 618 of apparatus 610. The top 640 comprises a rigid seal 641 along the periphery of the apparatus 610 that holds in place a flexible material 642 that extends across the top of chamber 618. The flexible material allows for interchangeable of various materials, including materials that have similar elastance as that of a human skull. The elastance of the skull or the materials used in these systems is the ratio of the change in pressure to the change in distance Examples of materials that may be used comprise silicone rubber of different thicknesses, e.g., 0.5, 1.0 and 1.5 mm; latex rubber; and Neoprene rubber.

Figure 7A:
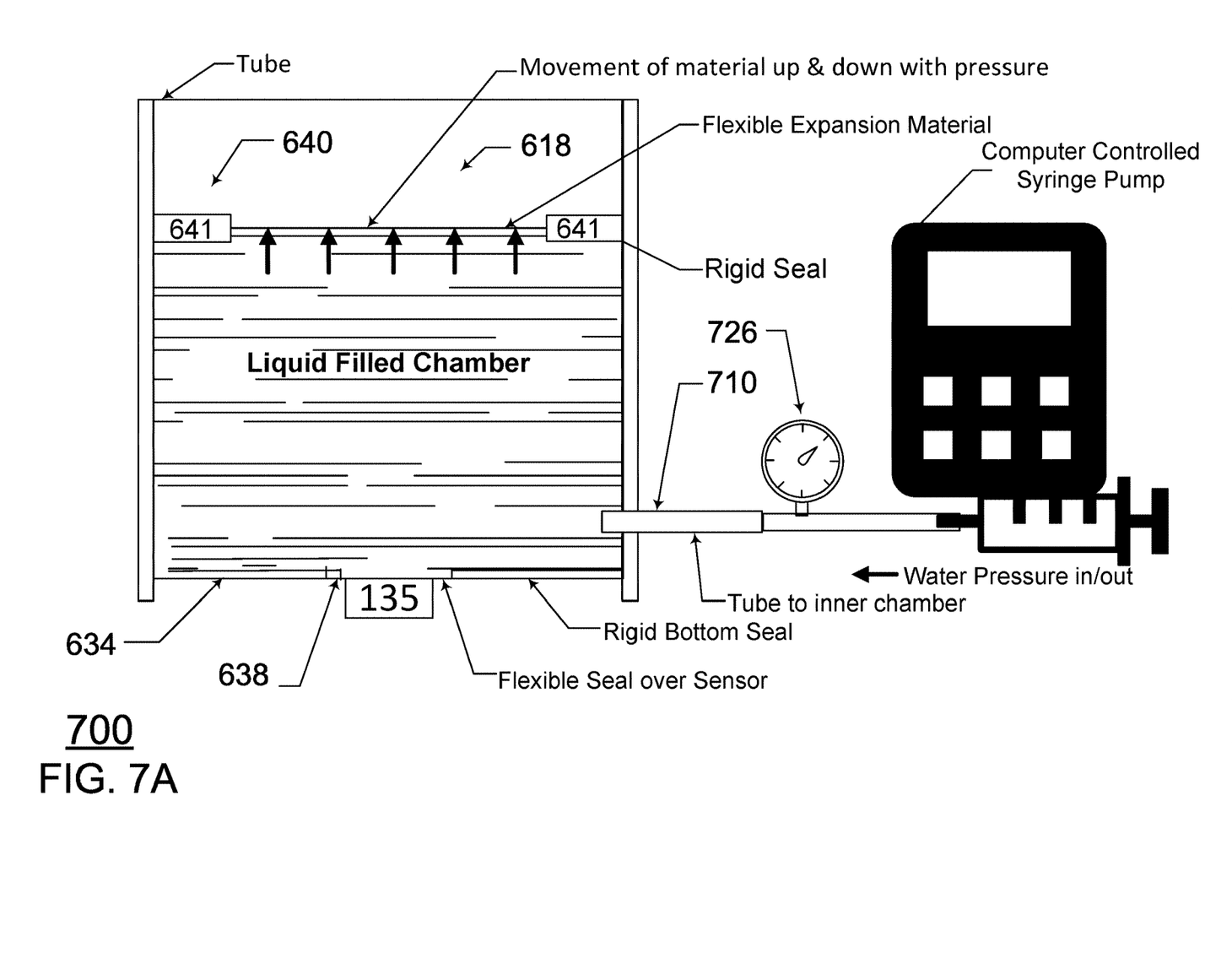
FIG. 7A is an example apparatus or system in accordance with one or more aspects of the disclosed technology.

FIG. 7A shows the apparatus 610 in a system 700 in accordance with aspects of the disclosed technology. The system 700 includes a tube 710 is inserted through a sidewall 628 (any sidewall would suffice) of apparatus 610. The tube 710 is filled with the liquid that also fills chamber 618. The tube 710 is coupled to a syringe pump 718 and a pressure gauge 726. Pump 718 can be used to control and change the timing and pressure exerted on flexible material 642. Pressure gauge 726 may then be used to measure the change in pressure within the chamber and that pressure is then correlated to the change in movement of flexible material 642 as measured by the sensor 135. For example, as previously discussed, if pressure gauge 426 comprises a pressure sensor with a voltage output, that voltage output may then be used to compare pressure changes with movement of the flexible material 642 and the output the ultrasound sensor 135.

Figure 7B:
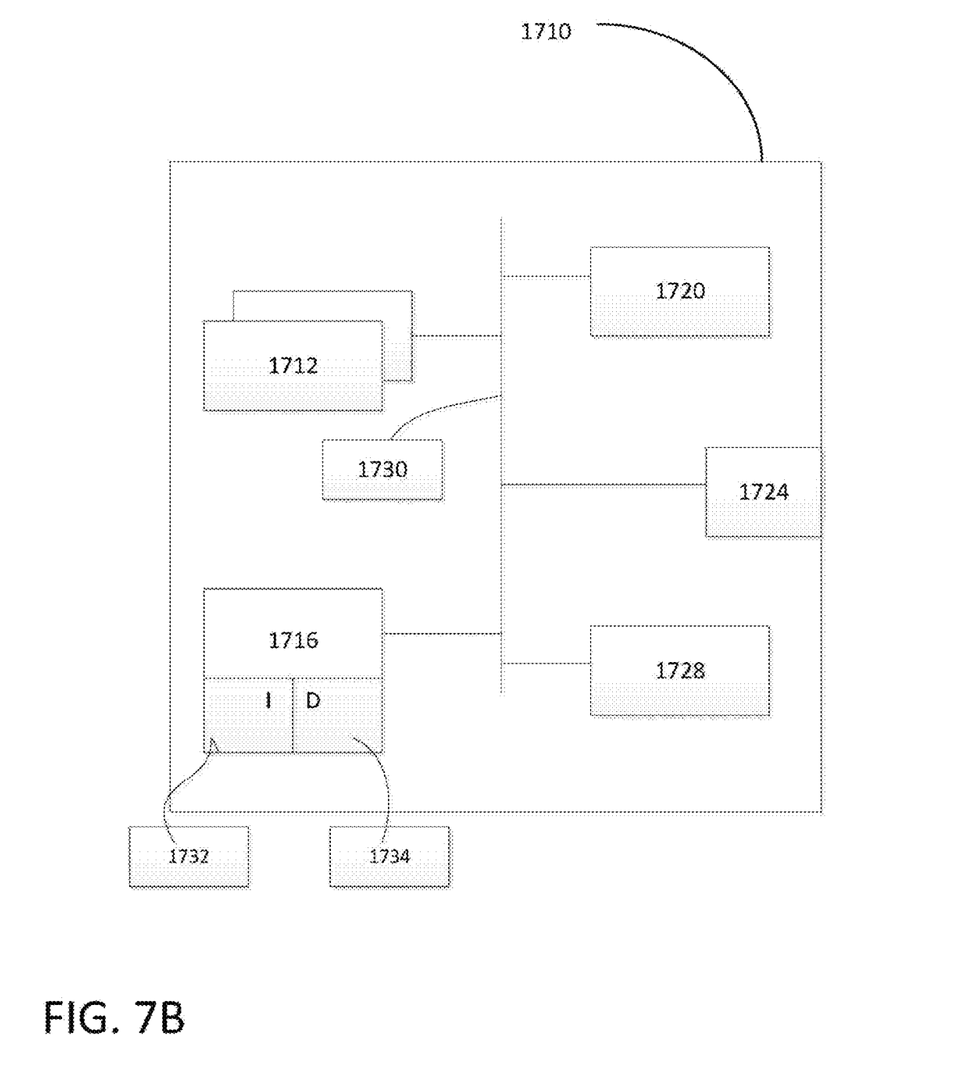
FIG. 7B is an example processing device or a processor based architecture in accordance with one or more aspects of the disclosed technology

Pump 718 may comprise a computer or processor controlled pump as shown in FIG. 7A. The computer or processor-controlled pump may be implemented in accordance with a computing device architecture as shown in FIG. 7B. As shown in FIG. 7B, computing device 1710 may include one or more processors 1712, memory 1716 storing data (D) and instructions (I), display 1720, communication interface 1724, and input system 1728, which are shown as interconnected via network 1730. Network 1730 may comprise data buses, etc., internal to a computer. Memory 1716 stores information accessible by the one or more processors 1712, including instructions 1732 and data 1734 that may be executed or otherwise used by the processor(s) 1712. The memory 1716 may be of any type capable of storing information accessible by the processor, including a computing device-readable medium, or other medium that stores data that may be read with the aid of an electronic device, such as a hard-drive, memory card, ROM, RAM, DVD or other optical disks, as well as other write-capable and read-only memories. Systems and methods may include different combinations of the foregoing, whereby different portions of the instructions and data are stored on different types of media.

The instructions 1732 may be any set of instructions to be executed directly (such as machine code) or indirectly (such as scripts) by the processor. For example, the instructions may be stored as computing device code on the computing device-readable medium. In that regard, the terms "instructions" and "programs" may be used interchangeably herein. The instructions may be stored in object code format for direct processing by the processor, or in any other computing device language including scripts or collections of independent source code modules that are interpreted on demand or compiled in advance. Processes, functions, methods and routines of the instructions are explained in more detail below.

The data 1732 may be retrieved, stored or modified by processor 1712 in accordance with the instructions 1732. As an example, data 1732 associated with memory 1716 may comprise data used in supporting services for one or more client devices, an application, etc. Such data may include data to support hosting web-based applications, file share services, communication services, gaming, sharing video or audio files, or any other network based services.

The one or more processors 1712 may be any conventional processor, such as commercially available CPUs. Alternatively, the one or more processors may be a dedicated device such as an ASIC or other hardware-based processor. Although FIG. 7B functionally illustrates the processor, memory, and other elements of computing device 1710 as being within the same block, it will be understood by those of ordinary skill in the art that the processor, computing device, or memory may actually include multiple processors, computing devices, or memories that may or may not be located or stored within the same physical housing.

Computing device 1710 may also include a display 1720 (e.g., a monitor having a screen, a touch-screen, a projector, a television, or other device that is operable to display information) that provides a user interface that allows for controlling the computing device 1710. Such control may include for example using a computing device to cause data to be uploaded through input system 1728 to the computing device for processing, as well relay control signals to another device such as the syringe shown in FIG. 7A. While input system 1728 may be used to upload data, e.g., a USB port, computing system may also include a mouse, keyboard, touchscreen or microphone that can be used to receive commands and/or data.

Figure 8:
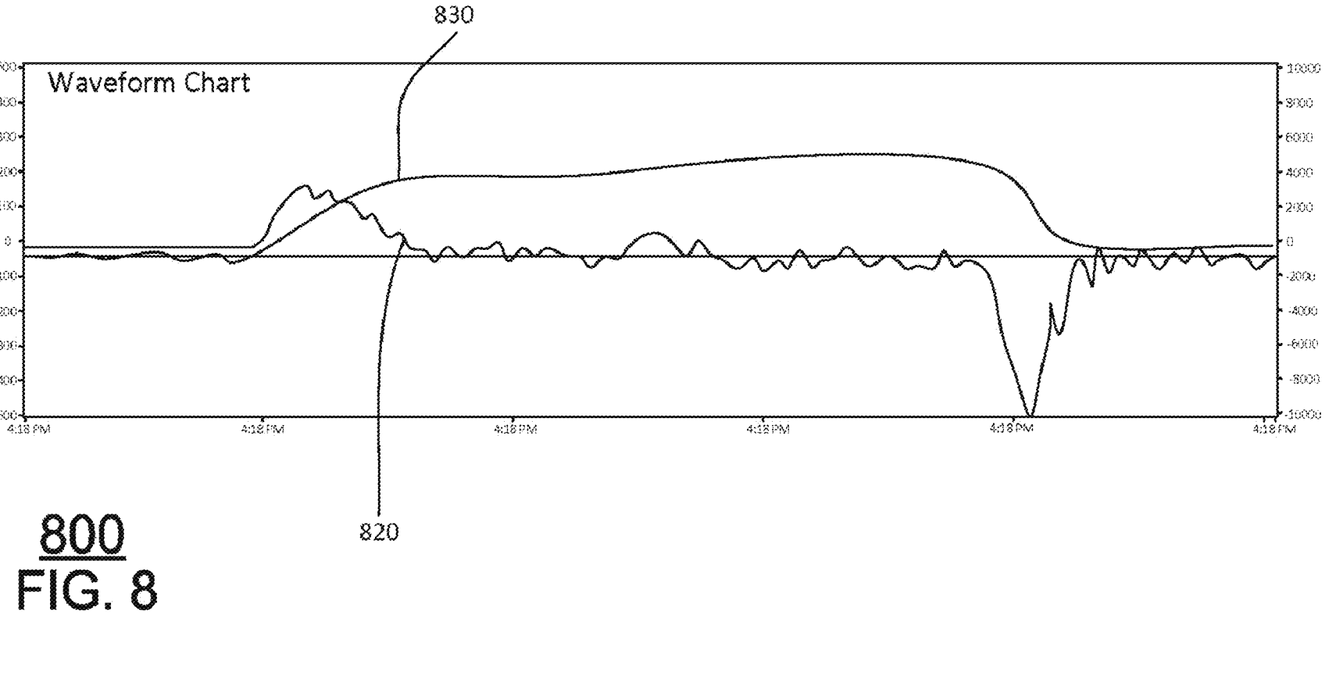
FIG. 8 is an example of a calibration signal in accordance with one or more aspects of the disclosed technology.

FIG. 8 shows an example of a trace of a measurement made by a sensor of PPLL using the systems previously described. The sensor was placed as described above and shown in the drawings at the location of sensor 135. The transmitted ultrasound tone is sent to the phantom. The first echo after the transmitted tone is received and amplified. This is compared to the phase of the transmitted tone. Because the phase varies during the echo the operator must decide where the "zero" point is. To do this in time a circuit called a "sample and hold" will hold the voltage at that point. This sample is sent to an analog to digital converter then to the computer. This signal is the 820 in FIG. 8.

Signal trace 830 is the integrated error signal (usually refed to as the "Integrated Error Output" or IEO) generated from phase data signal 820.

As shown in FIG. 8, at the first positive going wave of signal 820 on the left pressure was applied to the balloon or chamber. The signal 820 responded with an increase in amplitude, as did the integrated error signal 830. The signal 820 returned to neutral, but the integrated error signal 830 remained high. About halfway through the figure a smaller amount of pressure was applied and the amplitude of signal 820 increased as did the error signal 830. At the right-hand side of the figure, the pressure was relaxed, signal 820 went negative, as would be expected with removal of the pressure. The error signal 830 also declined and returned to the same level as it was before the pressure increase.

Figure 9:
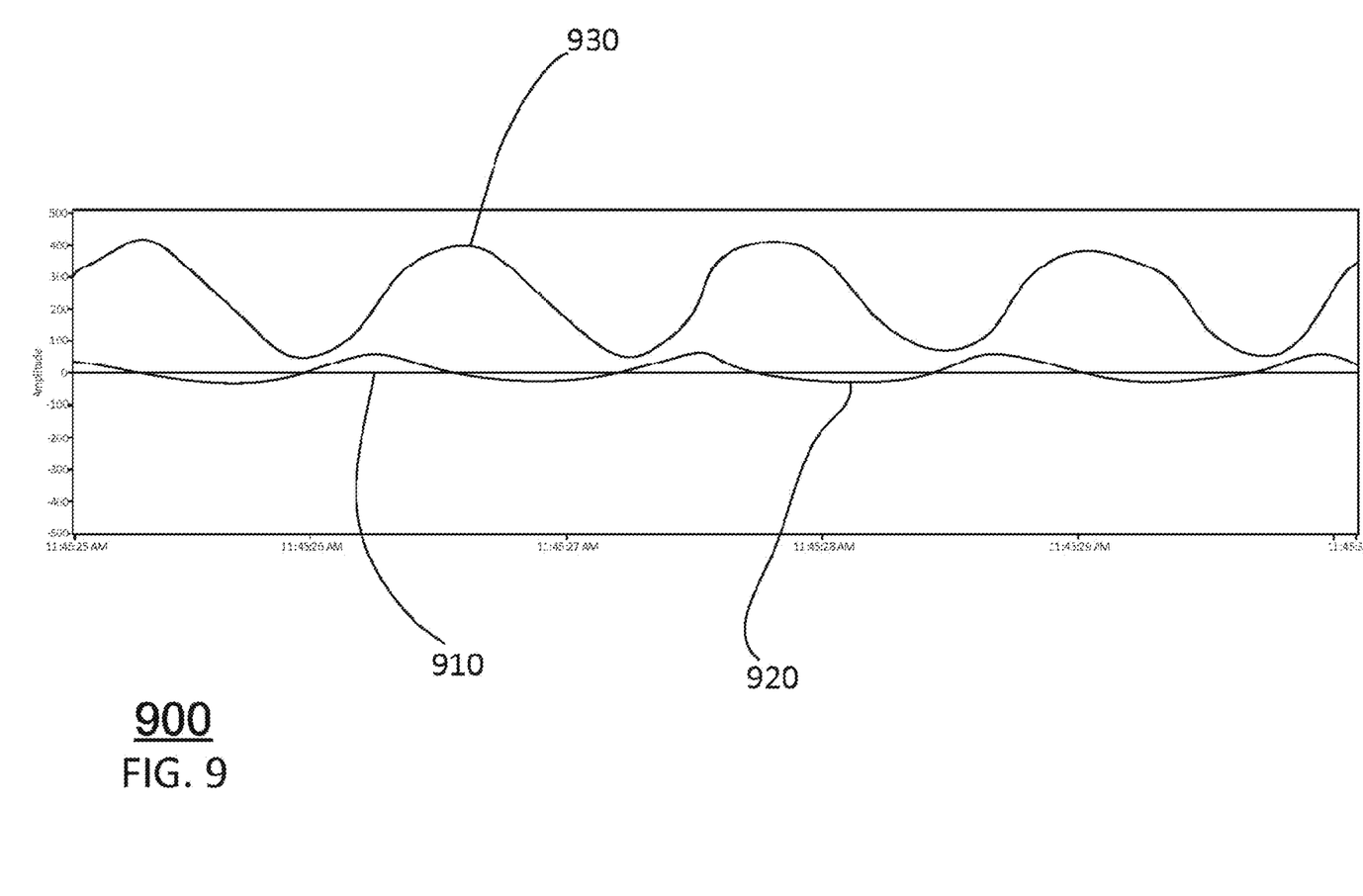
FIG. 9 is an example of a calibration signal in accordance with one or more aspects of the disclosed technology.

Using the setup as described in FIG. 7A and a computerized syringe pump it was possible to inject and withdraw water as to mimic the human skull. FIG. 9 shows the result. The repetition rate is about one second, a little slower than normal heart rate. The red line is the base 910. The phase data signal is the blue line 920. Infusion occurs in the first third of a second of the pulse. Withdrawing the same volume of fluid over the next two thirds of a second. Trace 930 shows the integrated error. This is a measurement of the change in distance across the chamber. This pressure can also be measured with the pressure gauge as a check on the system.

Figure 10:
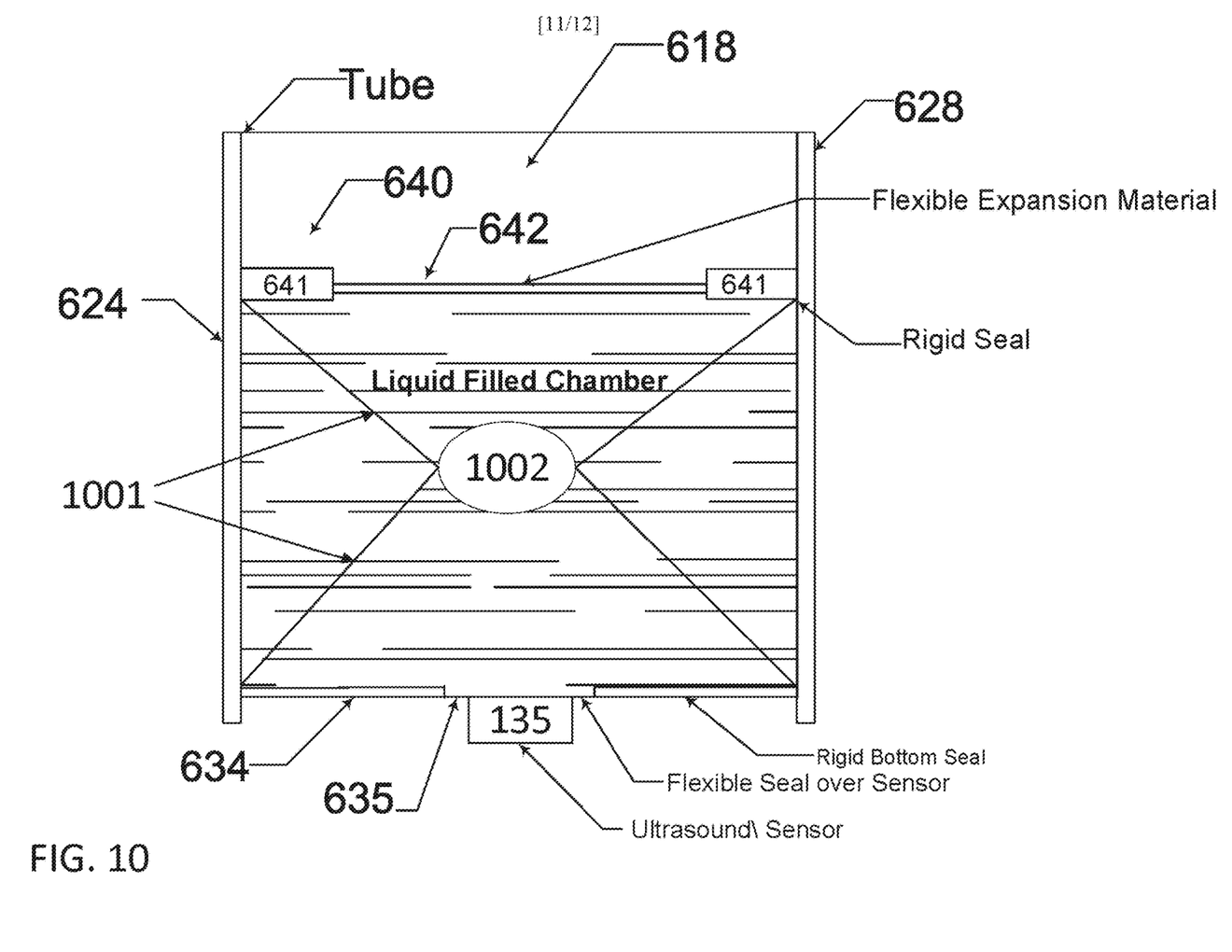
FIG. 10 is an example apparatus or system in accordance with one or more aspects of the disclosed technology.

While some of the foregoing examples assume an idealized view of the human skull, in reality, the brain would produce other reflections that have to taken into consideration. FIG. 10 shows one approach to adding these non-idealized structures to the phantom. A small balloon or thin walled container (1002) is placed within the structure. It is held in place by an array of strings (1001) to prevent it from moving. It would be filled with some material with a different density than water such as gelatin or agar. This would produce a reflection at the interfaces and would have a different velocity of sound then the surrounding media.

Figure 11:
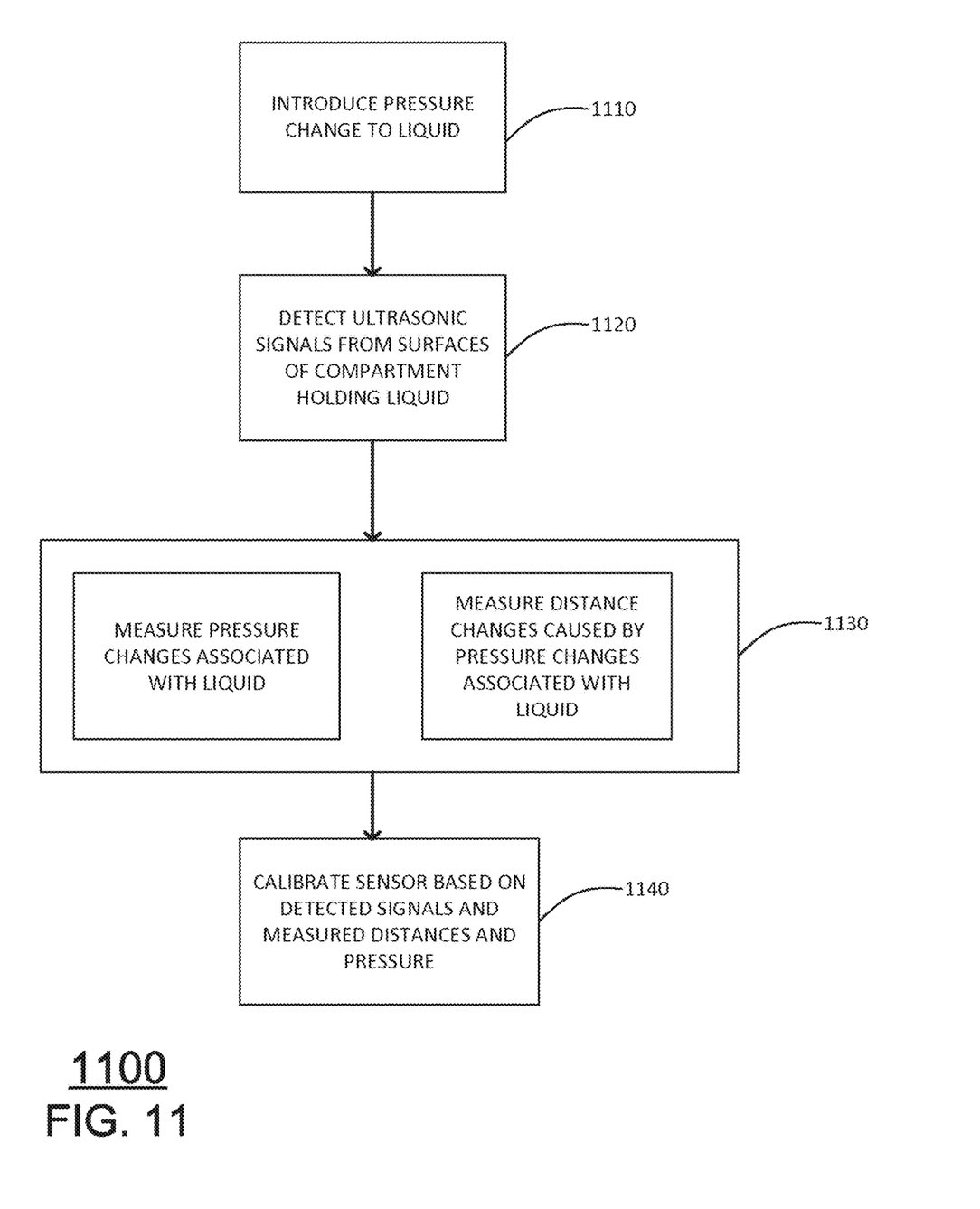
FIG. 11 shows an example method in accordance with one or more aspects of the disclosed technology.

FIG. 11 shows the steps of an example process or method in accordance with aspects of the disclosed technology. At block 1110, a pressure change is introduced or caused to be introduced into a liquid housed in a compartment. As explained above, the liquid may be contained within a balloon or occupy a volume created by the compartment. The pressure may be introduced using the mechanisms previously discussed, as well as other mechanisms.

At block 1120, a sensor is used to detect ultrasonic signals from surfaces of the compartment holding the liquid as discussed above. The sensor comprises a PPLL type sensor and detects phase changes in the ultrasonic signals which can be used to calculate a change in distance.

At block 1130, pressure and distance changes associated with the liquid are measured. These measurements may be done separately and need not be done simultaneously, or in a given order. In addition, detection of the ultrasonic signals at block 1120 and the measurements at block 1130, need not be done in the order shown.

At block 1140, the sensor used to detect the ultrasonic signal is calibrated based on the measured pressure and distance. For example, the distance calculated from the detection of the ultrasonic signals may be compared to the measured distances and compared to the pressure measurements. In this way, the calculated distances can be associated with pressure, and calibrated to pressure. As such, when the sensor is used in an actual ICP measurement, distances calculated from the ICP measurements may be more accurately correlated to pressure changes in the skull of the subject of the measurements.

Although different aspects of the invention herein have been described with reference to particular examples or embodiments, it is to be understood that these examples or embodiments are merely illustrative of the principles and applications of the present invention. It is therefore to be understood that numerous modifications may be made to the illustrative examples or embodiments and that other arrangements may be devised without departing from the spirit and scope of the present invention as defined by the appended claims.

The invention claimed is:

1. A calibration system for a pulsed phase-lock loop ultrasound measurement system, comprising:
   an apparatus having a compartment including:
      side surfaces defining a cavity of the compartment;
      an expandable elastic component for holding a liquid, the expandable elastic component positioned within the cavity of the compartment and having an elastance of a human skull; and
      an opening in one of the side surfaces by which a flow of the liquid between a source outside of the compartment and an interior of the expandable elastic component may be controlled, wherein the side surfaces are configured to confine a change in expansion of the expandable elastic component within the cavity along a primary axis;
   a sensor aligned with the cavity along the primary axis and arranged relative to the compartment to receive ultrasonic signals that reflect off an inner surface the expandable elastic component;
   a pressure gauge for measuring pressure of the liquid responsive to a change in flow of liquid between the source and the compartment; and
   a processing device for processing an integrated error signal output by the sensor indicative of a change in distance along the primary axis between the inner surface expandable elastic component and the sensor, wherein the change in distance is correlated to pressure changes of the liquid responsive to a change in flow of liquid between the source and the compartment.

2. The system of claim 1, comprising a pump coupled to a source of liquid.

3. The system of claim 2, wherein the pump comprises a syringe.

4. The system of claim 2, wherein the pump and pressure gauge are coupled to a controller, the controller controlling the timing of the pump to increase or decrease the pressure of the liquid in accordance with a cardiac cycle of a subject.

5. The system of claim 4, wherein the controller comprises the processing device.

6. The system of claim 4, wherein the controller comprises a second processing device distinct from the processing device.

7. The system of claim 1, wherein the expandable elastic component is a balloon that holds the liquid.

8. The system of claim 7, wherein the compartment is contoured to restrict movement of the balloon that holds the liquid in one direction relative to a side of the apparatus.

9. The system of claim 8, wherein the compartment includes a base, wherein the sensor is positioned in proximity to the base, and wherein the movement of the balloon is restricted in a direction along the primary axis towards the base.

10. The system of claim 1, wherein the compartment of the apparatus comprises a pair of side walls, a top and a bottom, the bottom including an area having a thin flexible membrane seal.

11. The system of claim 10, wherein the sensor is arranged proximate the thin flexible membrane seal.

12. The system of claim 1, wherein the pressure gauge comprises a pressure sensor having a voltage output signal, and the processing device correlates pressure changes indicated by the voltage output signal to a change in distance caused by movement of the liquid.

13. The system of claim 12, wherein the processing device correlates the change in distance to the integrated error output signal to calibrate the sensor.

14. A system for a pulsed phase-lock loop ultrasound measurement system, comprising:
   an apparatus having a compartment for holding a liquid, the compartment having an opening by which a flow of the liquid may be controlled;
   a sensor arranged relative to the compartment to receive ultrasonic signals that reflect off one or more inner surfaces of the compartment;
   a pressure gauge for measuring pressure of the liquid responsive to a change in flow of liquid between the source and the compartment; and
   a processing device for receiving an integrated error signal output by the sensor based on pressure changes of the liquid responsive to a change in flow of liquid between the source and the compartment,
   wherein the compartment of the apparatus comprises a pair of side walls, a top and a bottom, the bottom including an area having a thin flexible membrane seal,
   wherein the sensor is arranged proximate the thin flexible membrane seal, and
   wherein the top comprises a rigid seal around the periphery of the apparatus, the rigid seal supporting a flexible expandable material.

15. The system of claim 14, wherein the flexible expandable material comprises a material having elasticity that is equivalent to that of a human skull.

16. The system of claim 14, wherein the flexible expandable material moves in response to pressure changes in the pressure sensitive liquid.

17. A method for calibrating a pulsed phase-lock loop ultrasound measurement system, comprising:
   causing pressure changes to a liquid housed in an expandable elastic component positioned within a cavity of a compartment, the cavity defined by side surfaces of the compartment, the expandable elastic component having an elastance of a human skull, wherein the pressure changes cause a change in expansion of the expandable elastic component within the cavity along a primary axis that is confined by the side surfaces of the compartment;

detecting, by a sensor aligned with the cavity along the primary axis, ultrasonic signals that reflect off one or more inner surfaces of the compartment, the ultrasonic signals having information responsive to the pressure;

measuring pressure of the liquid responsive to the pressure changes; and processing an integrated error signal output by the sensor to calibrate the sensor indicative of a change in distance along the primary axis between the inner surface expandable elastic component and the sensor, wherein the change in distance is correlated to pressure changes of the liquid responsive to a change in flow of liquid between the source and the compartment.

18. The method of claim 17, wherein causing pressure changes comprises increasing or decreasing the pressure of the liquid by increasing or decreasing the flow of liquid into or out of the compartment.

19. The method of claim 17, wherein causing pressure changes comprises increasing or decreasing the pressure of the liquid in accordance with a cardiac cycle of a subject.

20. The method of claim 17, wherein processing comprises calculating one or more distance values based on the integrated error signal and comparing one or more measured changes in distance to at least one calculated distance value of the one or more calculated distance values.

* * * * *